(12) United States Patent
Witt et al.

(10) Patent No.: US 9,439,780 B2
(45) Date of Patent: Sep. 13, 2016

(54) ACETABULAR CUP INSERTER HANDLE

(75) Inventors: Tyler D. Witt, Warsaw, IN (US);
Austen Davenport, Columbia City, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 246 days.

(21) Appl. No.: 13/618,794

(22) Filed: Sep. 14, 2012

(65) Prior Publication Data

US 2014/0081278 A1 Mar. 20, 2014

(51) Int. Cl.
*A61F 2/46* (2006.01)
*A61B 17/92* (2006.01)
*A61F 2/30* (2006.01)

(52) U.S. Cl.
CPC .............. *A61F 2/4609* (2013.01); *A61B 17/92* (2013.01); *A61F 2002/30484* (2013.01); *A61F 2002/30565* (2013.01); *A61F 2002/4619* (2013.01); *A61F 2002/4681* (2013.01)

(58) Field of Classification Search
CPC ..................... A61F 2/4609; A61F 2002/4628; A61B 2017/00469; A61B 2017/00473; A61B 17/92
USPC ...................................................... 606/91, 99
See application file for complete search history.

(56) References Cited

U.S. PATENT DOCUMENTS

| | | | |
|---|---|---|---|
| 3,479,722 A * | 11/1969 | Maness | .................... B25B 27/24 |
| | | | 29/213.1 |
| 3,709,546 A * | 1/1973 | Vaughan | .................... B66C 1/54 |
| | | | 279/2.15 |
| 4,023,572 A | 5/1977 | Weigand et al. | |
| 4,716,894 A | 1/1988 | Lazzeri et al. | |
| 5,158,331 A * | 10/1992 | Wesselski | ............... F16B 2/185 |
| | | | 294/89 |
| 5,190,549 A * | 3/1993 | Miller | ................. A61B 17/1659 |
| | | | 606/104 |
| 5,236,433 A | 8/1993 | Salyer | |
| 5,443,471 A * | 8/1995 | Swajger | ............. A61B 17/1659 |
| | | | 403/294 |
| 5,540,697 A * | 7/1996 | Rehmann | .............. A61F 2/4609 |
| | | | 294/95 |
| 5,683,399 A * | 11/1997 | Jones | ........................ A61F 2/34 |
| | | | 606/91 |
| 5,954,727 A | 9/1999 | Collazo | |
| 6,626,913 B1 * | 9/2003 | McKinnon | .............. A61F 2/367 |
| | | | 606/86 R |
| 7,296,804 B2 | 11/2007 | Lechot et al. | |
| 7,396,357 B2 | 7/2008 | Tornier et al. | |
| 7,621,921 B2 | 11/2009 | Parker | |
| 7,682,363 B2 | 3/2010 | Burgi et al. | |
| 7,998,147 B2 | 8/2011 | Santarella et al. | |
| 8,303,601 B2 * | 11/2012 | Bandeira | .............. A61B 17/025 |
| | | | 606/90 |
| 8,449,548 B2 * | 5/2013 | Nelson | ............... A61B 17/1604 |
| | | | 606/86 R |
| 8,870,886 B2 * | 10/2014 | Burgi | ..................... A61B 17/56 |
| | | | 606/91 |
| 2005/0038443 A1 | 2/2005 | Hedley et al. | |
| 2006/0074418 A1 * | 4/2006 | Jackson | ............. A61B 17/7086 |
| | | | 606/914 |

(Continued)

FOREIGN PATENT DOCUMENTS

EP 1813229 A1 8/2007
EP 2345392 A1 7/2011

*Primary Examiner* — David Bates
(74) *Attorney, Agent, or Firm* — Schwegman Lundberg & Woessner, P.A.

(57) ABSTRACT

Disclosed is an acetabular positioning and insertion instrument. Additionally, a method of positioning an acetabular prosthesis with an insertion instrument is disclosed. The positioning instrument can include engaging members to contact an acetabular prosthesis and holding it relative to a portion of the instrument for both rotational and positioning of the prosthesis.

18 Claims, 4 Drawing Sheets

(56) References Cited

U.S. PATENT DOCUMENTS

| | | | |
|---|---|---|---|
| 2007/0093897 A1* | 4/2007 | Gerbec | A61F 2/4465 623/17.11 |
| 2009/0112219 A1 | 4/2009 | Daniels et al. | |
| 2009/0112220 A1 | 4/2009 | Kraus | |
| 2010/0049257 A1 | 2/2010 | Parker | |

* cited by examiner

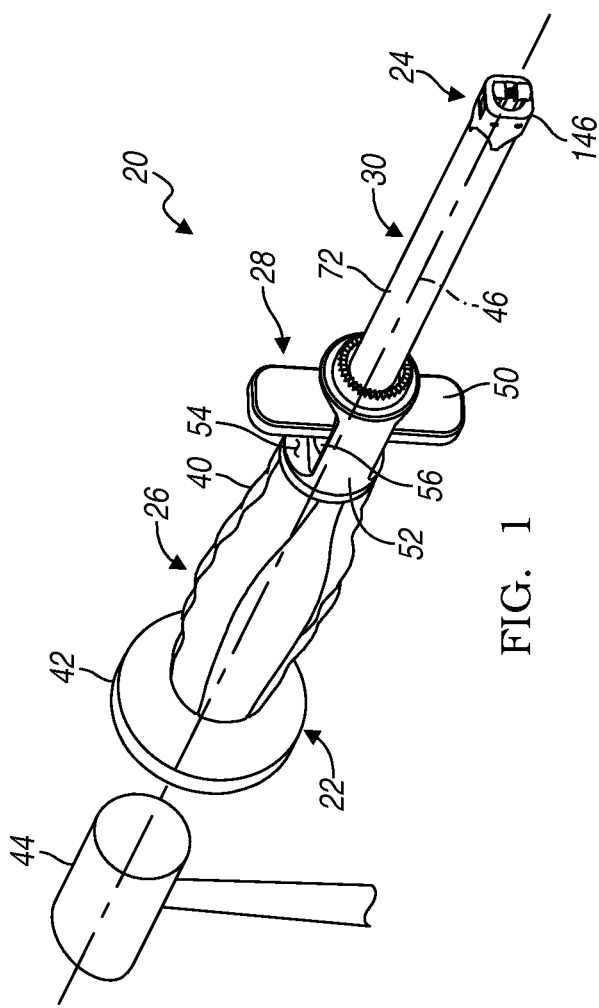
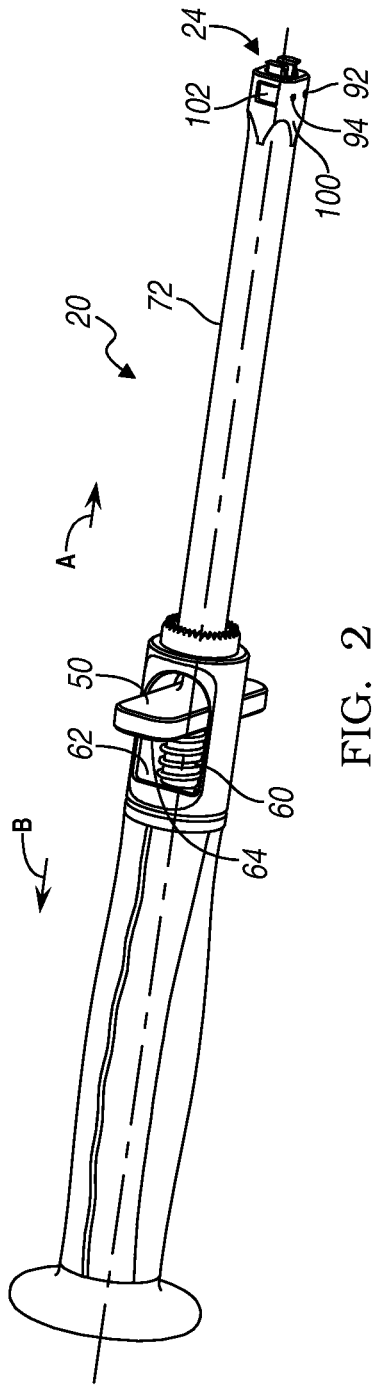
FIG. 1
FIG. 2

ACETABULAR CUP INSERTER HANDLE

FIELD

The subject disclosure relates to systems and methods for positioning a prosthesis in a subject, and particularly relates to an instrument and methods for engaging and inserting an acetabular prosthesis in a subject.

BACKGROUND

This section provides background information related to the present disclosure which is not necessarily prior art.

In performing a procedure on a patient, a prosthesis can be used to replace or augment a natural anatomical feature. For example, due to age, injury, disease, or other causes, a portion of the anatomy may need to be replaced or resurfaced. Examples include replacing an acetabulum on a patient either in conjunction with or separate from replacing or resurfacing a femoral head. An acetabular prosthesis is generally positioned within a prepared acetabulum.

Positioning an acetabular prosthesis within a prepared acetabulum can include various dexterous movements of the prosthesis because the acetabular prosthesis is generally positioned within the acetabulum in a selected alignment and position. The alignment of the acetabular prosthesis is generally selected to be relative to the natural anatomy where a central axis of the acetabular prosthesis must be aligned or is selected to be aligned with a portion of the natural anatomy. In positioning the acetabular prosthesis in the selected position, both position and axial alignment can be selected.

Along with position and axial alignment, the acetabular prosthesis also needs to be engaged into the acetabulum with a selected force to ensure proper seating and positioning of the acetabular prosthesis. Thus, the acetabular prosthesis is generally required to be held in the selected position and alignment during an impaction. Accordingly, positioning the acetabular prosthesis generally requires dexterity on the part of the user, such as a surgeon, to position the acetabular prosthesis appropriately in a patient's anatomy.

SUMMARY

An acetabular prosthesis can be positioned in an anatomy, such as a human anatomy, to replace or repair a natural acetabulum. The natural acetabulum may need to be replaced due to injury or disease and can be prepared to receive an acetabular prosthesis according to generally understood methods. For example, the acetabulum can be reamed with a selected reamer. A prosthetic acetabulum can then be implanted into the prepared acetabulum.

The prosthetic acetabulum can be engaged near an apical hole or region of the acetabular prosthesis to be held for positioning into the prepared acetabulum. The acetabular prosthesis can be held with an instrument that includes moveable or expanding jaws or fingers to engage the acetabular prosthesis. The moveable fingers can be expanded to engage the apical region of the acetabular prosthesis and then can be disengaged from the acetabular prosthesis to allow for removal of the instrument after implantation of the acetabular prosthesis. The fingers can be engaged and disengaged by biasing the fingers outwardly towards the acetabular prosthesis and removing the biasing force to allow them to collapse to disengage from the acetabular prosthesis. An instrument that holds the acetabular prosthesis can also be impacted to position and fix the acetabular prosthesis into the prepared acetabulum.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 1 is a first perspective view on an acetabular positioning instrument;

FIG. 2 is a second perspective view of the acetabular insertion instrument;

Corresponding reference numerals indicate corresponding parts throughout the several views of the drawings.

DETAILED DESCRIPTION

Figure 3A:
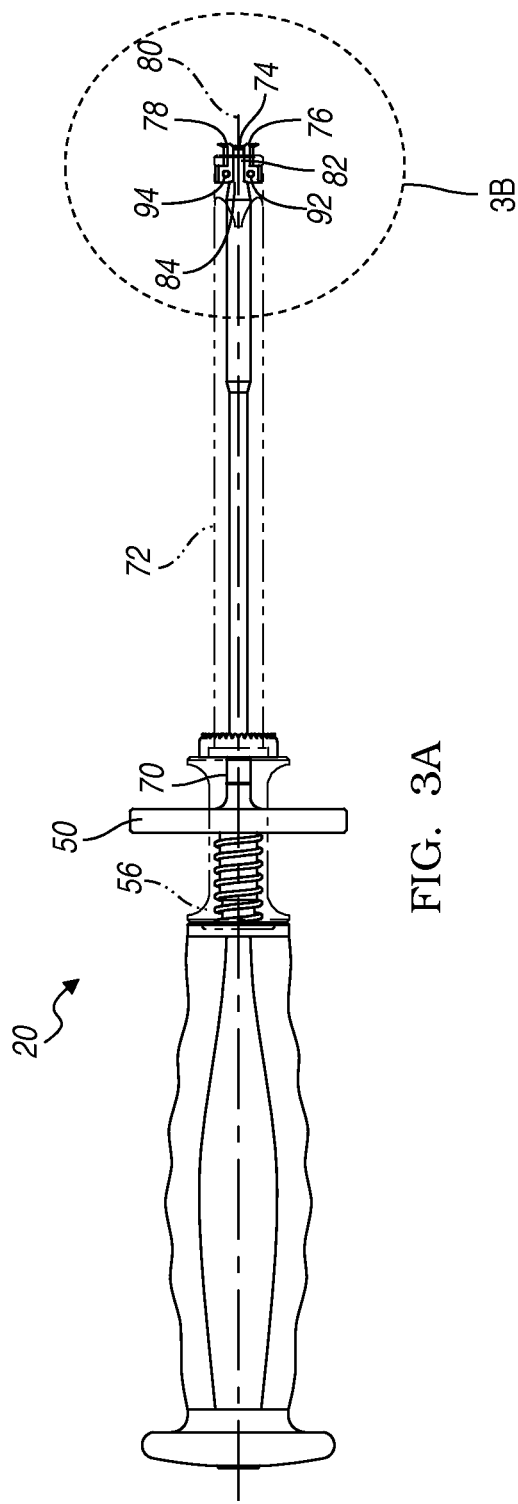
FIG. 3A is an elevational view of the acetabular insertion instrument.

With reference to FIGS. 1 and 2, an acetabular inserter handle assembly 20 is illustrated. The inserter handle assembly 20, also referred to as an acetabular inserter handle or inserter handle, can include a first impaction or distal end 22 and a second or proximal prosthesis engagement end 24. Between the two ends 22, 24, is a handle or grasping portion 26, a manipulation or biasing region 28, and an extension or holding tubular region 30.

The handle region 26 can include a graspable portion 40 to be held by a user or a user's hand during impaction and manipulation of an acetabular prosthesis (FIG. 4 of 130), as discussed further herein. The inserter handle 20 can be used to engage an acetabular prosthesis and the user can engage or hold the handle 40 to manipulate the handle assembly 20 with one hand. A second hand of the user or an assistant's hand can be used to impact an impaction portion 42 such as with a mallet or hammer 44. The handle or grasping portion 40 can include ridges or a knurled surface or other appropriate friction or grasping region to allow for a user to securely hold the handle assembly 20 during the manipulation of an acetabular prosthesis. The mallet 44 engaging or impacting the impaction end 42 can drive or provide a force along a longitudinal axis 46 of the inserter assembly 20. The longitudinal axis 46 of the inserter assembly 20 can generally define an axis or a line along which a force is transferred from the impact end 42 to the engaging end 24, as discussed further herein.

The biasing region 28 can include a moveable member 50, that can also be referred to as a biasing lever or plate that can have at least two portions or ears extending from the biasing region 28. The moveable member 50 can extend from a housing or chassis portion 52 through openings or windows 54 formed in one or more regions of the chassis 52. The windows 54 can be defined by a wall or walls 56 of the chassis member 52.

Within the chassis portion 52, a biasing spring or member 60 can be positioned between a distal wall or first wall 62 and the moveable member 50. The moveable member 50 can define a surface 64. The biasing member 60 can include a compression or spiral spring that is positioned between the two surfaces 62, 64 to bias the moveable member 50 generally in the direction of the proximal end 24 in the direction of arrow A. As discussed further herein, the biasing of the moveable member 50 can assist in holding and positioning an acetabular prosthesis relative to the inserter handle 20. The biasing member 60 can be any appropriate biasing member such as a resilient material, including a natural or artificial rubber, or other appropriate material or device that provides a biasing force onto the surface 64 in the direction of arrow A to hold a prosthesis or selected member relative to the inserter handle 20.

Figure 3B:
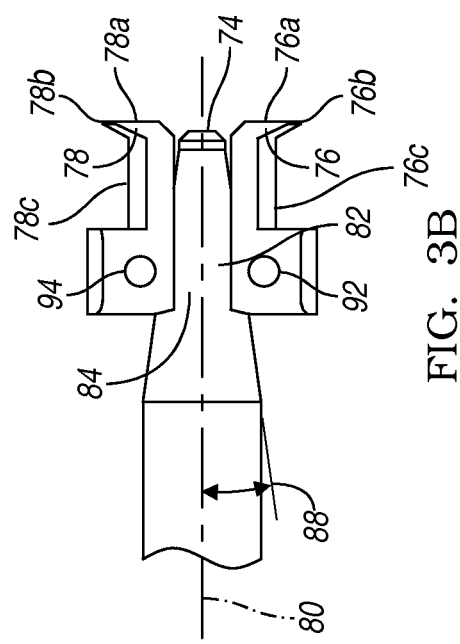
FIG. 3B is a detail elevational view of an end the acetabular insertion instrument of FIG. 3A.

The moveable member 50 can be moved by a user against the biasing force of the compression spring member 60 such that the member 50 moves towards the distal end 22 generally in the direction of arrow B, as illustrated in FIG. 2. With continuing reference to FIG. 2, and additional reference to FIGS. 3A and 3B, the member 50 is connected to a rod or moveable member 70 that passes through a cannula or bore of a tube 72 towards the proximal end 24 of the handle assembly 20. As illustrated in FIGS. 3A and 3B, the tube 72 is shown in phantom to illustrate the length of the rod 70. The rod 70 can extend from the member 50 towards the proximal end 24 and can have a proximal end 74. The proximal end 74 can be positioned between two fingers or projections 76 and 78 to bias the two fingers 76, 78 apart, which can also be away from a central axis 80 of the rod 70. Thus, the rod 70 can be an adjusting member to bias the fingers 76, 78 away from one another in an expanded position.

The rod 70 can include a ramp or slanted surface that includes tapering outer edges 82 and 84 that tapers at an angle 88 relative to the central axis 80. Accordingly, when the rod 70 is biased in the direction of arrow A, that is when the member 50 is biased in the direction of Arrow A by the biasing member 60, the fingers 76, 78 are biased away from the central axis 80. When the rod 70 is moved in the direction of arrow B, when the member 50 is moved against or forced against the compression member 60, the biasing force is no longer present between fingers 76, 78 and the fingers can move toward the central axis 80.

The fingers 76, 78, can therefore move in two directions. In the first direction when they are biased and in a biased position, the fingers 76, 78 are in an expanded position such that an outer dimension of the fingers or at least a portion thereof, defines a maximum or large outer dimension. When the rod 70 is moved out of the biasing position, such as when the member 50 is moved in the direction of arrow B, the fingers 76, 78 are allowed to collapse or move towards one another and the central axis 80. In the collapsed position, the fingers 76, 78 define an outer dimension that is less than the expanded dimension. In a collapsed position, the fingers 76, 78 may disengage a member, as discussed further herein.

The fingers 76, 78 can each include an axle or pivoting region or member 92, 94 that allows the respective fingers 76, 78 to rotate towards the central axis 80 or away from the central axis 80. During the rotation, the proximal ends 76a, 78a, of the respective fingers, 76, 78 can move away from or towards the central axis 80. The proximal ends 76a, 78a can further include respective projections 76b, 78b or portions that extend from an outer surface 76c, 78c to allow for a positive engagement with a prosthesis, such as an acetabular prosthesis, as discussed further herein. With particular reference to FIG. 2, the cylinder or tube 72 can include an outer wall 100 through which the axles or rotating portions 92, 94 can extend to provide a fixed axis of rotation for each of the respective fingers 76, 78. Openings 102 in the outer wall 100 can also allow portions of the fingers to extend to further contact portions of the wall 100.

Figure 4A:
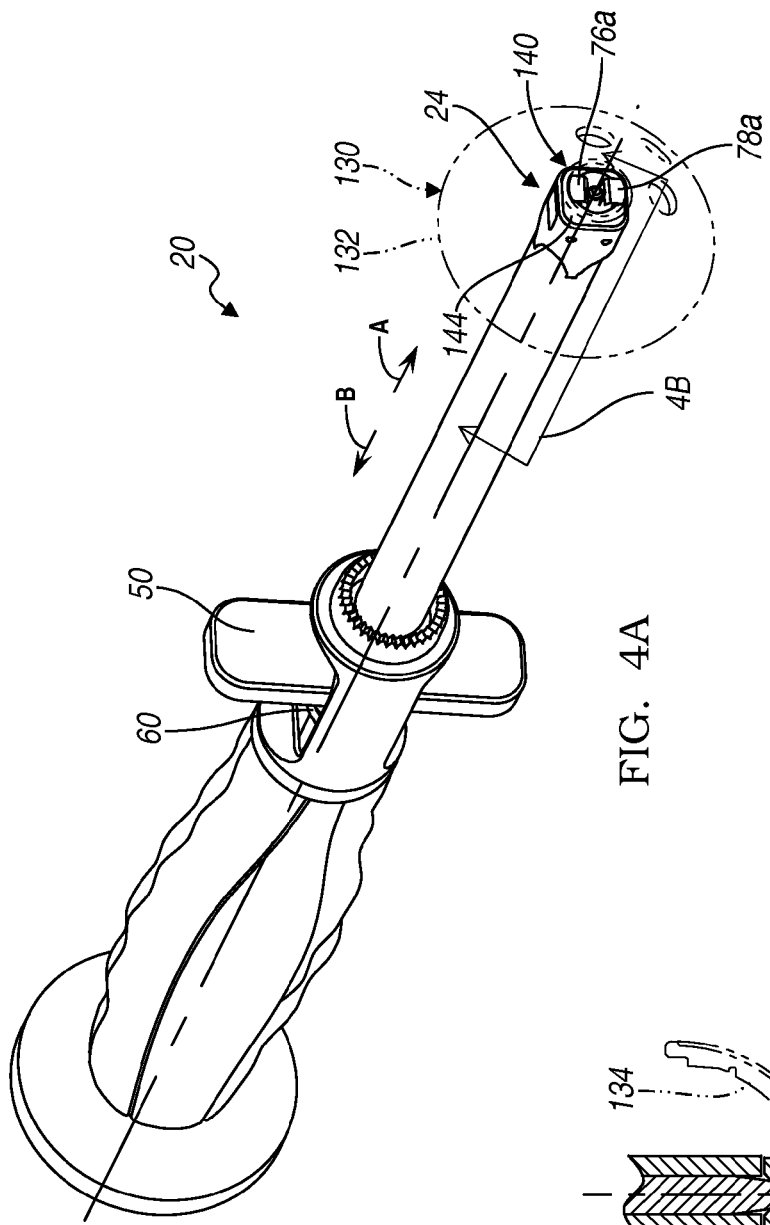
FIG. 4A is a third perspective view of the acetabular insertion instrument engaging an acetabular prosthesis.
Figure 4B:
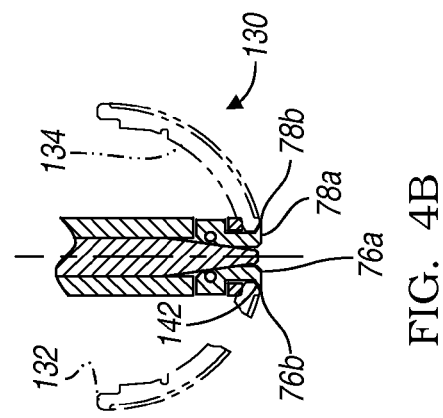
FIG. 4B is a cross-sectional detail view of the acetabular insertion instrument engaging an acetabular prosthesis of FIG. 4A.

The inserter handle 20 can be used to engage an acetabular prosthesis 130, as illustrated in FIG. 4. The acetabular prosthesis can include a distal or upper rim 132 that defines an opening to an interior 134 of the acetabular prosthesis 130. The interior of the acetabular prosthesis 134 can include an apical opening or passage 140. The apical opening 140 can be an open bore or a blind bore into the acetabular prosthesis 130. According to various embodiments, the acetabular prosthesis 130 can include an apical bore through which a fixation screw or implantation handle, such as the handle assembly 20, can engage the acetabular prosthesis 130. It is understood, however, that the insertion handle 20 need not pass through the acetabular prosthesis 130, therefore a through bore is not necessary in the acetabular prosthesis 130. Nevertheless, the acetabular prosthesis 130 can define an undercut or depression 142 that can be engaged by the projections 76b, 78b and/or ends 76a, 78a of the fingers 76, 78.

As illustrated in FIG. 4, the proximal projections 76b, 78b of the fingers 76, 78 project into the undercut 142 of the acetabular prosthesis 130 when the rod 70 is biased in the direction of arrow A and the proximal end 74 is positioned between the fingers 76, 78 to bias them away from the central axis 80 and into the undercut 142. The acetabular prosthesis 130 can further include a non-circular or keyed opening 144, such as a square opening near the apical opening 140, to engage a square or proximal edge 146 as illustrated in FIG. 1. The keyed or non-circular proximal edge 146 engaged in the opening 144 can fix rotation of the acetabular prosthesis 130 relative to the proximal end 24 of the inserter handle 20. The acetabular prosthesis 130 can, therefore, be held rotationally and axially relative to at least the proximal end 24 of the inserter handle.

Figure 5:
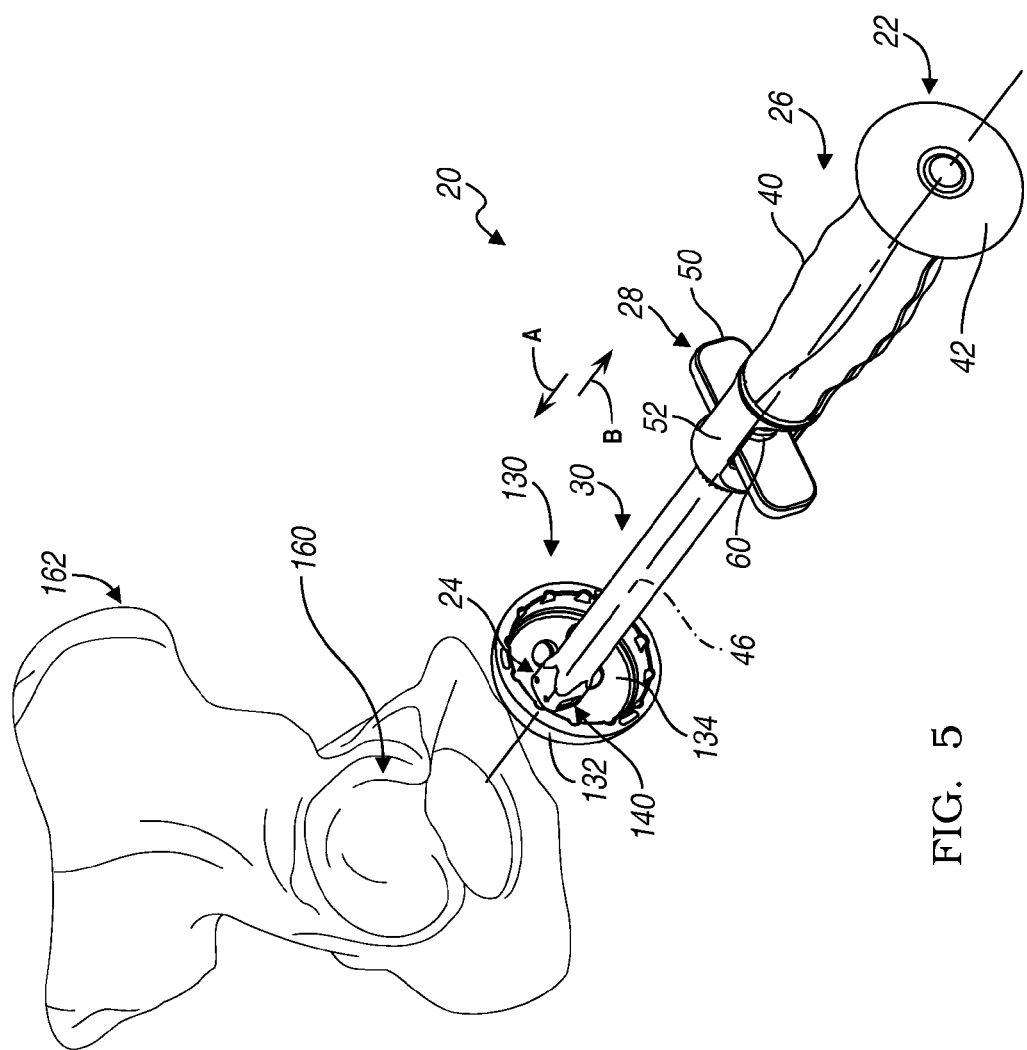
FIG. 5 is an environmental view of an acetabular insertion instrument positioning an acetabular prosthesis into a pelvis.

As illustrated in FIG. 4, the rod 70 is biased in the direction of arrow A, which can also be referred to as the bias direction, by the biasing member 60, as illustrated in FIG. 3A. When the acetabular prosthesis 130 is connected to the handle assembly 20, as illustrated in FIG. 4, the handle assembly 20 can be used to implant the acetabular prosthesis 130 into a prepared acetabulum 160 of a selected pelvis 162, as illustrated in FIG. 5. The acetabular prosthesis 130 can be held with the inserter handle 20 due to engagement of the fingers 76, 78, in the biased position of the rod 70, with the acetabular prosthesis 130.

The inserter assembly 20 can then be disengaged from the acetabular prosthesis after positioning it relative to the prepared acetabulum 140 by moving the member 50 against the biasing member 60 to move the rod 70 out of engagement and the biased position with the fingers 76, 78. Once the rod 70 is moved out of engagement with the fingers 76, 78, the fingers 76, 78 can move towards the central axis 80 to disengage the undercut 142 of the acetabular prosthesis 130. The fingers 76, 78 move to the unbiased position to disengage from the prosthesis 130. Once disengaged, the inserter handle 20 can be removed from the acetabular prosthesis 130 to allow for a completion of a procedure. Completing the procedure can include reduction of a femoral head of a femur or a femoral head of a prosthesis, positioning of a bearing within the acetabular prosthesis 130, and/or closing the patient.

Once the handle assembly 20 is disengaged from the acetabular prosthesis 130, it can be reengaged with the acetabular prosthesis 130 by moving the rod 70 and the member 50 against the biasing member 60 to allow the fingers 76, 78 to move towards the central axis 80. When the fingers 76, 78 move towards the central axis 80, the fingers 76, 78, including the projections 76b, 78b can be moved into the central or apical bore 140, including the undercut 142. The member 50 can then be disengaged to allow the member 50 and the rod 70 to be biased in the direction of arrow A such that the rod 70 biases the fingers 76, 78 away from the central axis 80. When biased, the projections 76b, 78b move into the undercut 142 to engage the acetabular prosthesis 130. Accordingly, after the handle assembly 20 is used to position the acetabular prosthesis 130 into the prepared acetabulum 160 of the pelvis 162, the inserter assembly 20 can also be used to disengage the positioned acetabular prosthesis 130 from the prepared acetabulum 160. The fingers 76, 78 include projections 76b, 78b to allow for the positioning and removal of the inserter assembly 20 in a substantially axial direction only without requiring rotation of the inserter assembly 20 to engage and disengage the acetabular prosthesis 130. Accordingly, the inserter assembly 20 can be used to efficiently engage the acetabular prosthesis 130 to position the acetabular prosthesis 130 and for removal of the acetabular prosthesis 130.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A system for positioning an acetabular prosthesis into a subject, the system comprising:
    a graspable portion extending from a first end to a second end;
    a moveable projection extending from the graspable portion;
    a biasing member contacting a first wall of the graspable portion and a second wall of the moveable projection and biasing the moveable projection in a longitudinal direction to a first biased position;
    a biasing rod interconnected with the moveable projection at a first end portion and moveable into a rod biasing position when the moveable projection is biased into the first biased position, the biasing member and biasing rod centered around a common longitudinal axis, wherein a second end portion of the biasing rod is tapered and a tip of the biasing rod has a smaller diameter than a body of the biasing rod;
    a tube extending from the second end of the graspable portion, the biasing rod moveable within the tube; and
    at least one holding finger connected to the tube and moveable from a second biased position to an unbiased position;
    wherein moving the biasing rod into the rod biasing position biases the at least one holding finger into the second biased position such that the at least one holding finger is biased away from the common longitudinal axis of the biasing rod;
    wherein the biasing rod engages an internal surface of the at least one holding finger.

2. The system of claim 1, further comprising:
    an impaction surface defined by the first end of the graspable portion;
    wherein the moveable projection is near the second end of the graspable portion.

3. The system of claim 1, wherein the moveable projection and the biasing rod are fixedly interconnected so that movement of the moveable projection moves the biasing rod.

4. The system of claim 3, wherein the biasing member is a resilient member and biases both the moveable projection and the biasing rod in a first direction away from the first end of the graspable portion to the first biased position and the rod biasing position.

5. The system of claim 1, wherein the at least one holding finger includes an axis of rotation member that engages a wall of the tube.

6. The system of claim 5, wherein the at least one holding finger includes a first holding finger and a second holding finger;
    wherein the biasing rod biases the first holding finger apart from the second holding finger when the biasing rod is in the rod biasing position.

7. The system of claim 6, wherein when the biasing rod is removed from the rod biasing position the first holding finger is substantially free to move towards the second holding finger.

8. The system of claim 7, further comprising:
    an acetabular prosthesis;
    wherein when the first holding finger and the second holding finger are apart they engage the acetabular prosthesis and when the first holding finger and the second holding finger disengage the acetabular prosthesis they are in the unbiased position.

9. A system for positioning an acetabular prosthesis into a subject, the system comprising:
    a graspable portion extending from a first end to a second end;
    a moveable member extending external to the graspable portion;
    a tube extending from the second end of the graspable portion;
    a first biasing member contacting both a first wall of the graspable portion and a second wall of the moveable member to bias the moveable member in a first direction;
    a second biasing member interconnected with the moveable member and extending from the second end of the graspable member and through at least a portion of the tube, wherein the second biasing member is movable into a first position when the movable member is biased in the first direction, the first and second biasing members centered around a common longitudinal axis; and
    a first finger and a second finger both connected to the tube and moveable between a first close position wherein the first finger and the second finger are a first distance from one another to a second spaced position wherein the first finger and the second finger are a second distance from one another,
    wherein the second distance is greater than the first distance;

wherein moving the second biasing member into the first position advances the second biasing member towards an end of the first and second fingers to position the second biasing member between the first finger and the second finger and bias the first finger and the second finger into the second spaced position;

wherein the first biasing member operably biases the second biasing member to bias the first finger and the second finger in the second spaced position; and wherein a first in between the tube and the first finger and a second pin between the tube and the second finger facilitate movement of the first and second fingers between the first close position and the second spaced position.

10. The system of claim 9, wherein a second end of the second biasing member has a tapered end tip to bias the first finger and the second finger apart to the second spaced position to the second distance.

11. The system of claim 10, wherein the moveable member is configured to be moved against the first biasing member in a second direction to move the second biasing member in the second direction to allow the first finger and the second finger to move toward the first close position.

12. The system of claim 11, wherein the second biasing member is positioned between the first finger and the second finger at the first position when the first finger and the second finger are in the second spaced position and is removed to a second position to allow the first finger and the second finger to move to the first close position.

13. The system of claim 10, wherein the first finger includes a first finger projection extending away from the first finger and the second finger includes a second finger projection extending away from the second finger.

14. The system of claim 13, further comprising:

an acetabular prosthesis including a bore at or near an apex of the acetabular prosthesis that includes an undercut, wherein the bore is spaced from a rim of the acetabular prosthesis;

wherein at least one of the first finger projection or the second finger projection is configured to engage the undercut of the acetabular prosthesis.

15. The system of claim 14, wherein the second biasing member biases the first finger and the second finger into the second spaced position to hold the first finger projection and the second finger projection into the undercut.

16. A system for positioning an acetabular prosthesis into a patient, the system comprising:

a handle portion;

a movable member;

a tube extending from the movable member;

a biasing member connecting the handle portion and the movable member, the biasing member configured to bias the movable member to at least a first biased position;

a rod connected to the movable member at a first end portion and at least partially contained within and movable in the tube, the rod moveable into at least a rod biasing position when the movable member is biased into the first biased position; and a pair of holding fingers, each holding finger connected to the tube and movable between a first position in which the fingers are separated by a first distance and a second position in which the fingers are separated by a second distance greater than the first distance, wherein the second end portion of the rod is tapered and a tip of the biasing rod has a smaller diameter than a body of the rod, wherein moving the rod into the rod biasing position places the rod between the pair of holding fingers to bias the holding fingers into the second position, and wherein each holding finger includes a pin that allows for pivotal movement of each holding finger toward and away from a central axis of the rod.

17. The system of claim 16, wherein each holding finger includes a projection extending away from the holding finger, each projection configured to engage an acetabular prosthesis.

18. The system of claim 17, wherein the projection on each of the holding fingers is configured to engage an undercut in a bore at or near an apex of the acetabular prosthesis.

* * * * *

UNITED STATES PATENT AND TRADEMARK OFFICE
CERTIFICATE OF CORRECTION

| | |
|---|---|
| PATENT NO. | : 9,439,780 B2 |
| APPLICATION NO. | : 13/618794 |
| DATED | : September 13, 2016 |
| INVENTOR(S) | : Witt et al. |

Page 1 of 1

It is certified that error appears in the above-identified patent and that said Letters Patent is hereby corrected as shown below:

In Column 6, Line 11, in Claim 3, delete "claim 1 ," and insert --claim 1,--, therefor In Column 6, Line 65, in Claim 9, after "another,", delete "¶", therefor In Column 7, Line 10, in Claim 9, delete "in" and insert --pin--, therefor Signed and Sealed this
Third Day of July, 2018

Andrei Iancu
*Director of the United States Patent and Trademark Office*